United States Patent [19]

Narula et al.

[11] Patent Number: 5,041,422

[45] Date of Patent: Aug. 20, 1991

[54] ADAMANTANE DERIVATIVE, COMPOSITIONS OF MATTER CONTAINING SAME, PROCESSES FOR PREPARING SAID ADAMANTANE DERIVATIVE AND SAID COMPOSITION AND ORGANOLEPTIC AND DEODORANCY USED OF SAID ADAMANTANE DERIVATIVE AND SAID COMPOSITION

[75] Inventors: Anubhav Narula, Hazlet, N.J.; Carlos Benaim, Bedford Hills, N.Y.

[73] Assignee: Flavors & Fragrances Inc. International, New York, N.Y.

[21] Appl. No.: 635,234

[22] Filed: Dec. 28, 1990

[51] Int. Cl.$^5$ ................................................. A61K 7/46
[52] U.S. Cl. ...................................... 512/19; 568/818; 252/174.11; 131/276; 424/76.4
[58] Field of Search ........................... 512/19; 568/818; 252/174.11; 424/76.4

[56] References Cited

U.S. PATENT DOCUMENTS 3,356,739 12/1967 Schneider ............................ 568/818
3,996,169 12/1976 Light et al. ............................ 512/19

OTHER PUBLICATIONS

Grob et al., Helv. Chim. Acta, vol. 68, pp. 760–769 (1985).
Mlinaric-Malerski et al., J.A.C.S., vol. 105, pp. 7389–7395 (1983).

*Primary Examiner*—James H. Reamer
*Attorney, Agent, or Firm*—Arthur L. Liberman

[57] ABSTRACT

Described are hydroxy adamantane compounds and derivatives thereof and a process for preparing same.

6 Claims, 3 Drawing Sheets

GLC PROFILE FOR EXAMPLE I.

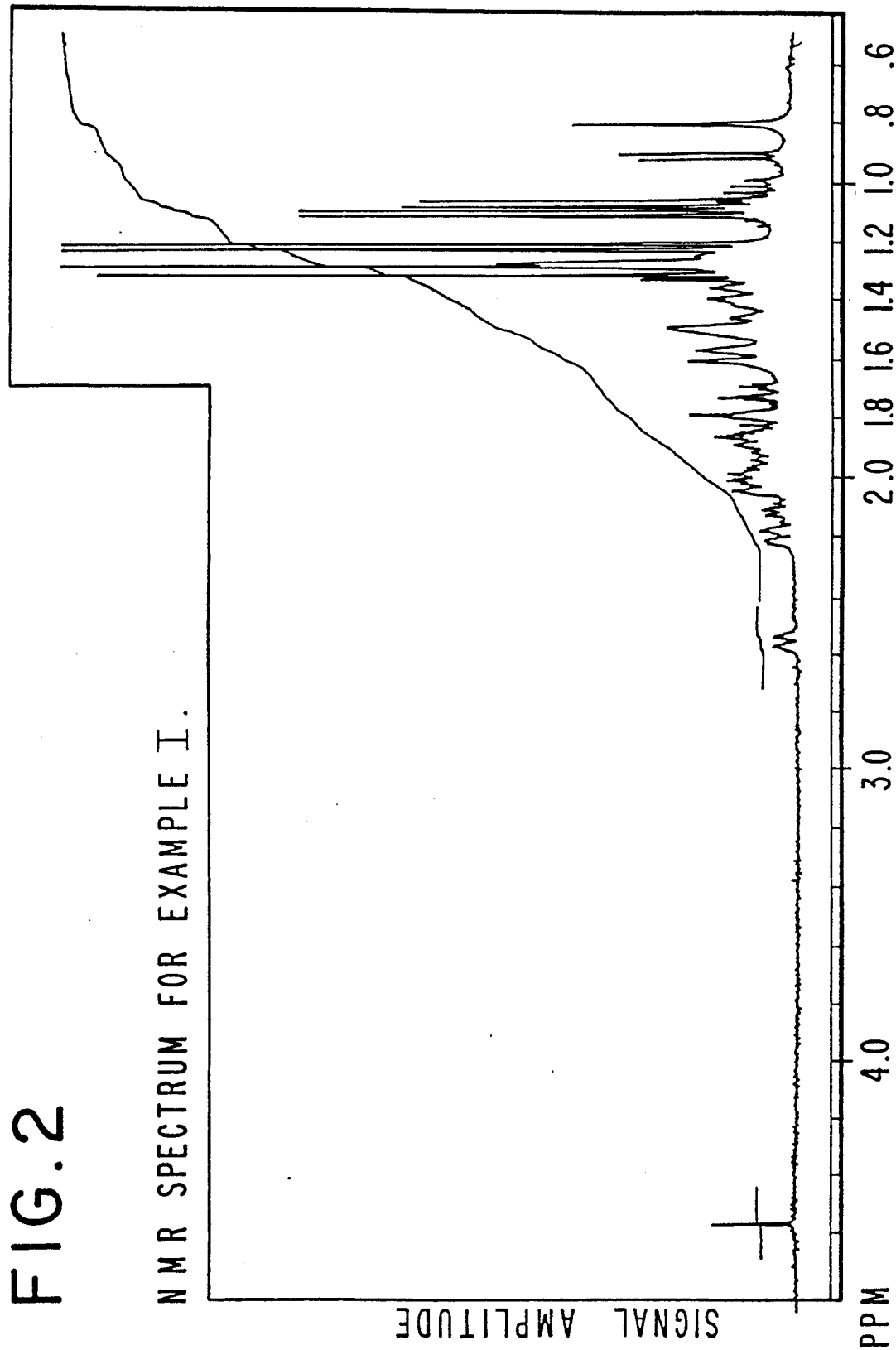
FIG. 2 NMR SPECTRUM FOR EXAMPLE I.

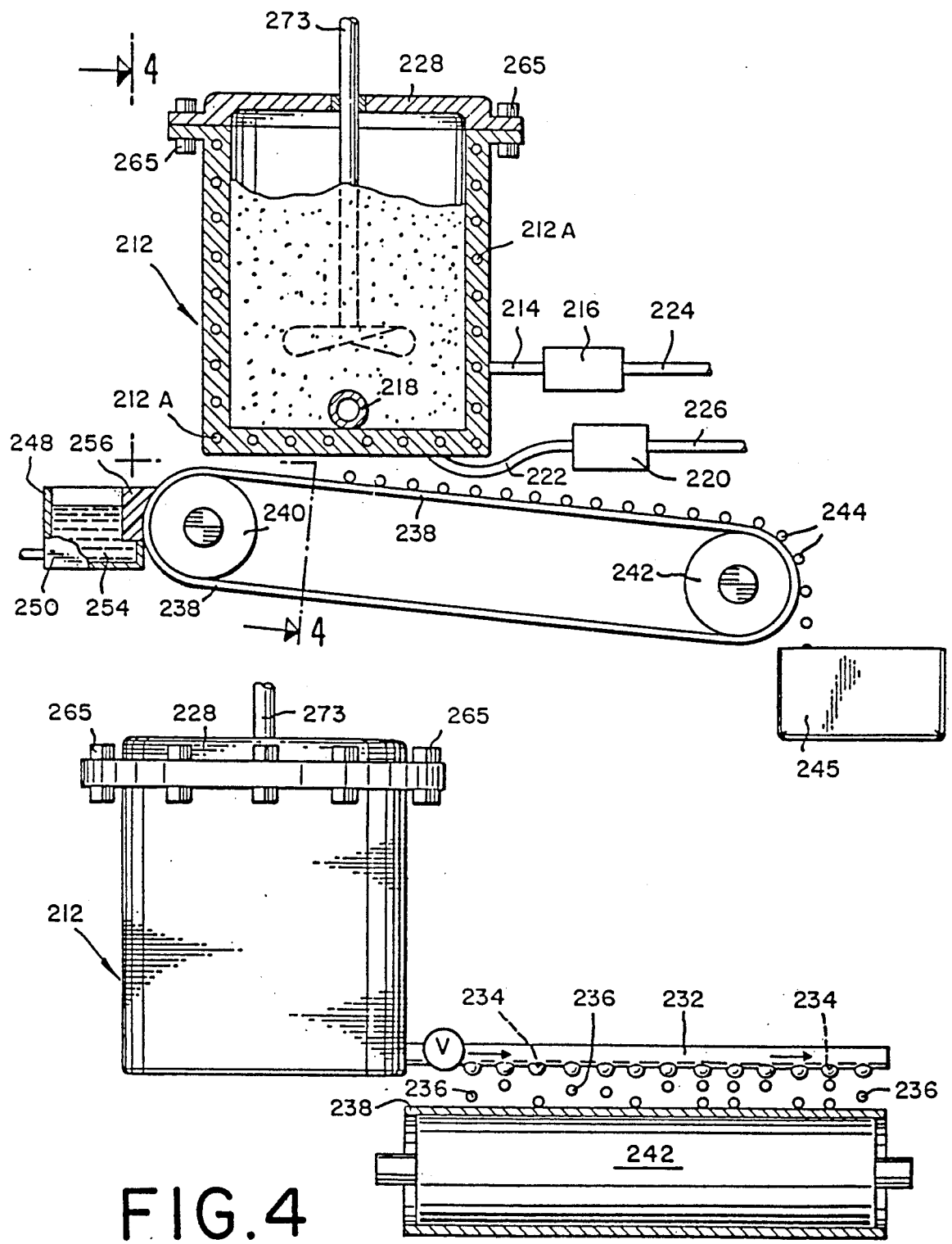

ADAMANTANE DERIVATIVE, COMPOSITIONS OF MATTER CONTAINING SAME, PROCESSES FOR PREPARING SAID ADAMANTANE DERIVATIVE AND SAID COMPOSITION AND ORGANOLEPTIC AND DEODORANCY USED OF SAID ADAMANTANE DERIVATIVE AND SAID COMPOSITION

BACKGROUND OF THE INVENTION

Hydroxy adamantane derivatives are known in the prior art as taught by Grob, et al., Helv. Chim. Acta., 1985, 68(3), pp. 760-769 and Mlinaric-Majerski et al., J. Am. Chem. Soc., 1983, 105, p. 7389-7395 as well as Fort & Schleyer; "Adamantane: ... ", Chem. Rev., 1984, 64, pp. 277-300.

However, the adamantane derivative having the structure:

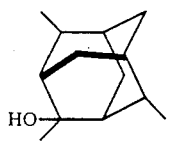

is a novel compound and has unexpected, unobvious, advantageous and valuable perfumery properties. These properties have hitherto been unknown with such substantivity and strength.

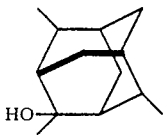

Figure 1:
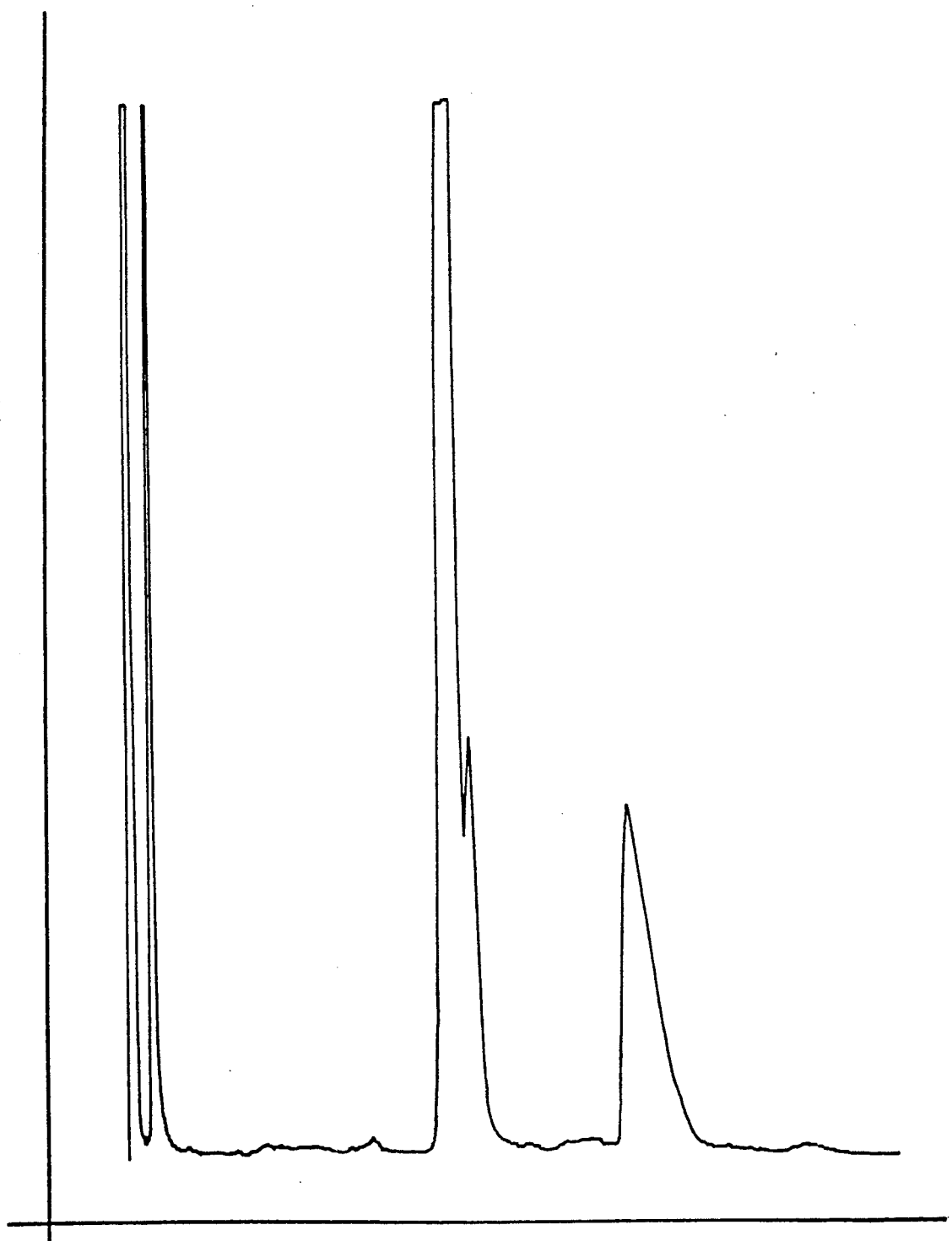
FIG. 1 is the GLC profile for the reaction product of Example I containing the compound having the structure.

FIG. 2 is the NMR spectrum for the compound having the structure;

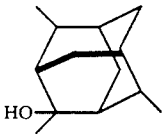

produced according to Example I.

FIG. 3 is a cut-away side elevation view of apparatus used in producing polymeric fragrances containing the compound having the structure:

of our invention.

FIG. 4 is the front elevation view of the apparatus of FIG. 3 looking in the direction of the arrows along lines 4—4 of FIG. 3.

DETAILED DESCRIPTION OF THE DRAWINGS

Referring to FIGS. 3 and 4, in particular, the apparatus used in producing polymeric fragrances containing the adamantane derivative comprises a device for forming scented polyolefin (for example) pellets, which comprises a vat or container 212 into which a mixture of polyolefins such as polyethylene and an aromatic substance or scented material is placed (e.g., the adamantane derivative of our invention). The container is closed by an airtight lid 228 and clamped to the container by bolts 265. A stirrer 273 traverses the lid or cover 228 in an airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 saybolt seconds and having a melting point in the range of 200°-280° F. The heater 212A is operated to maintain the upper portion of the container 212 within a temperature range of from 250°-350° F. The bottom portion of the container is heated by means of heating coils 212A heated through a control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scented aroma imparting material (e.g., the adamantane derivative of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5-30% by weight of the scented material (e.g., the adamantane derivative of our invention) is added to the polyolefin.

After the scent imparting material (e.g., a composition containing the adamantane derivative of our invention) is added to the container 212, the mixture is stirred for a few minutes, for example, 5-15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., the adamantane derivative of our invention) will continuously drop through orifices 234 downwardly from conduit 232. During this time the temperature of the polymer (e.g., polyethylene or polyolefin) and scent imparting material (e.g., the adamantane derivative of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., the adamantane derivative of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

THE INVENTION

Our invention relates to the compound having the structure:

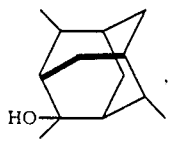

uses thereof in augmenting or enhancing the aroma of perfume compositions, colognes and perfumed articles and the intermediate for producing same having the structure:

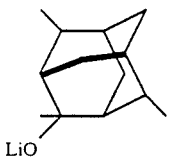

The compound having the structure:

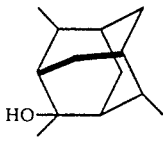

has an intense and substantive patchouli, rich, natural, woody, spicy, and ginger aroma profile.

The compound having the structure:

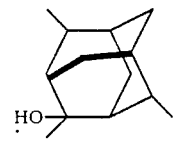

was prepared by carrying out the reaction, to wit:

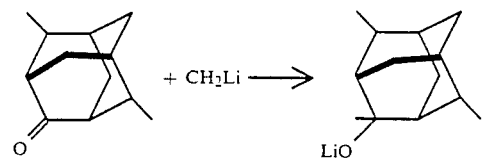

followed by the reaction, to wit:

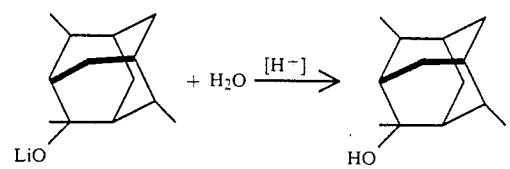

The precursor compound, that is the precursor ketone having the structure:

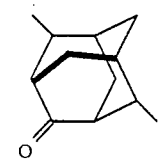

can be prepared according to Example XII at Columns 90 and 91 of U.S. Pat. No. 4,956,481 issued on Sept. 11, 1990.

The compound having the structure:

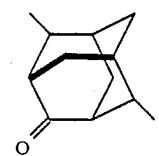

may be reacted with methyl lithium to form the intermediate having the structure:

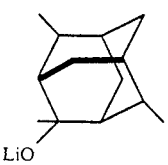

a novel compound itself. The intermediate having the structure:

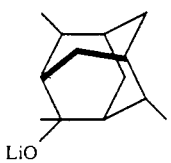

is then hydrolyzed in the presence of weak acid such as hydrochloric acid to form the compound of our invention having the structure:

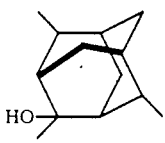

The reactions used to prepare the compound having the structure:

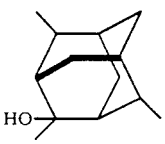

are as follows:

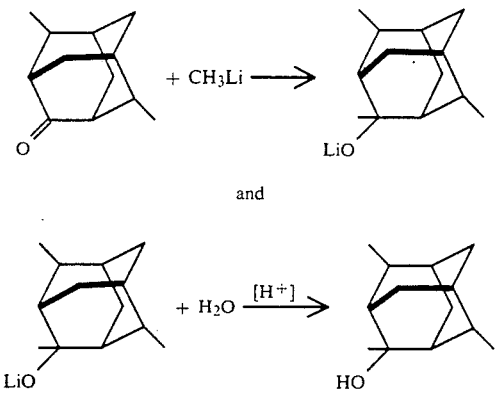

As an olfactory agent, the adamantane derivative of our invention can be formulated into or used as a component of a "perfume composition" or can be used as a component of a "perfumed article" or the perfume composition may be added to perfumed articles.

The term "perfume composition" is used herein to mean a mixture of organic compounds including, for example, alcohols (other than the hydroxy-substituted adamantane derivative of our invention); aldehydes, ketones, nitriles, ethers, lactones, natural essential oils, synthetic essential oils, and frequently hydrocarbons which are admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, the individual component will contribute its particular olfactory characteristics, but the overall effect of the perfume composition will be the sum of the effects of each of the ingredients. Thus, the adamantane derivative of this invention can be used to alter the aroma characteristics of a perfume composition, for example, by highlighting or moderating the olfactory reaction contributed by another ingredient in the composition.

The amount of the adamantane derivative of this invention which will be effective in perfume compositions depends on many factors including the other ingredients, their amounts, and the effects which are desired. It has been found that perfume compositions containing as little as 0.5% of the adamantane derivative of our invention or even less can be used to impart interesting and substantive patchouli, rich, natural, woody, spicy and ginger aroma nuances to soaps, liquid and solid, anionic, cationic, nonionic, and zwitterionic detergents, cosmetic powders, liquid and solid fabric softeners, optical brightener compositions, perfumed polymers and other products. The amount employed can range up to 50% or higher and will depend on considerations of cost, nature of the end product and the effect desired on the finished product and the particular fragrance sought.

The adamantane derivative of this invention can be used alone or in a perfume composition as an olfactory component in detergents and soaps, space odorants and deodorants; colognes, toilet waters, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of the adamantane derivative of our invention will suffice to impart interesting, substantive and strong patchouli, rich, natural, woody, spicy and ginger aromas. Generally, no more than 0.5% is required.

In addition, the perfume composition can contain a vehicle or carrier for the adamantane derivative taken alone or taken together with other ingredients. The vehicle can be a liquid such as an alcohol such as ethanol, a glycol such as propylene glycol or the like. The carrier can be an absorbent solid such as a gum, (e.g., gum arabic, guar gum and xanthan gum) or components for encapsulating the composition such as gelatin which can be used to form a capsule wall surrounding the perfume oil as by means of coacervation.

An additional aspect of our invention provides an organoleptically improved smoking tobacco product and additives therefor including methods of making the same which overcome problems heretofore encountered in the creation or enhancement of specific desired sweet, oriental notes. Such notes both prior to and on smoking in both the main stream and the side stream, may now be readily controlled and maintained at the desired uniform level regardless of variations in the tobacco components of the blend, or the nature of the filter used in conjunction with the smoking tobacco article.

This invention further provides improved tobacco additives for materials used in the fabrication of tobacco articles (particularly smoking tobacco articles) and methods whereby desirable sweet, oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient the adamantane derivative of our invention.

In addition to the adamantane derivative of our invention other flavoring and aroma additives may be added to the smoking tobacco material or substitute therefor either separately or in admixture with the adamantane derivative of our invention, to wit:

I. SYNTHETIC MATERIALS

Beta-methylcinnamaldehyde;
Eugenol;
Dipentene;
Damascenone;
Maltol;
Ethyl maltol;
Delta-undecalactone;
Delta-decalactone;
Benzaldehyde;
Amyl acetate;
Ethyl butyrate;
Ethyl valerate;
Ethyl acetate;
2-Hexen-1-ol;
2-Methyl-5-isopropyl-1-3-nonadiene-8-one;
2-Methyl-5-isopropylacetophenone;
2-Hydroxy-2,5,5,8a-tetramethyl-1-(2-hydroxyethyl)-decahydronaphthalene;
Dodecahydro-3a,6,6,9a-tetramethylnaphtho(2,1-Beta)-furan;
4-Hydroxy hexanoic acid, gamma-lactone;
Polyisoprenoid hydrocarbons defined in Example V of U.S. Pat. No. 3,589,372 issued on June 29, 1971.

II. NATURAL OILS

Celery seed oil;
Coffee extract;
Bergamot oil;
Nutmeg oil; and
Origanum oil.

An aroma and flavoring concentrate containing the adamantane derivative of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased or blended tobacco material or reconstituted tobacco material or tobacco substituted (e.g., lettuce leaves) or mixtures thereof. The proportions of flavoring additives may be varied in accordance with taste, but insofar as enhancement or the imparting of sweet, oriental, "Turkish"-like notes prior to and on smoking, in both the main stream and the side stream, we have found that satisfactory results are obtained if the proportion by weight of the sum total of adamantane derivative to smoking tobacco material is between 50 ppm and 150 ppm (0.005%–0.15%) of the active ingredients to the smoking tobacco material. We have further found that satisfactory results are obtained if the proportions by weight of the sum total of adamantane derivative used to flavoring material is between 0.005:1 and 0.50:1. volatile organic solvents and the resulting solution may either be sprayed on a cured, cased and blended tobacco material; or the tobacco material or filter may be dipped into such solution. Under certain circumstances a solution of the adamantane derivative of our invention taken alone or taken further together with other flavoring additives are set forth, supra, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus-treated tobacco may be blended with other tobaccos before the ultimate tobacco product is formed. In such cases, the tobacco treated may have, e.g., the adamantane derivative of our invention in excess of the amounts of concentration above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated, supra, e.g., the adamantane derivative of our invention can be incorporated with materials such as filter tip materials, seam paste, packaging materials and the like which are used along with the tobacco to form a product adapted for smoking. Furthermore, the adamantane derivative of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant part or substituted materials or both.

It will thus be apparent that the adamantane derivative of our invention can be utilized to alter, modify, augment or enhance sensory properties, particularly organoleptic properties, such as flavor(s) and/or fragrance(s) of a wide variety of consumable materials.

In accordance with one specific example of our invention, an aged, cured and shredded domestic burley tobacco is sprayed with a 20% alcohol solution of the the compound having the structure:

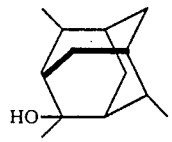

in an amount to provide a tobacco composition containing 800 ppm by weight of the compound having the structure:

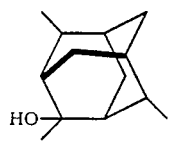

on a dry basis. Thereafter the alcohol is removed by evaporation and the tobacco is manufactured into cigarettes by the usual techniques. The cigarette when treated as indicated has a desired and pleasant aroma which is detectable in the main stream and in the side stream when the cigarette is smoked. The aroma is described as being oriental, natural Turkish tobacco-like with pleasant and long-lasting cigar box-like nuances.

Our invention also relates to the utilization of controlled release technology for the controlled release of perfumes into gaseous environments; odor maskants and deodorizing agents into gaseous environments; and tobacco aromatizing and flavors into smoking article filters from polymers such as mixtures of epsilon caprolactone polymers and polyethylene.

The method of incorporating the adamantane derivative of our invention or perfume compositions containing same into polymers may be according to the technique of U.S. Pat. No. 3,505,432 issued on Apr. 7, 1970 (the specification for which is incorporated by reference herein) or U.S. Pat. No. 4,274,498 issued on Jan. 27, 1981, the disclosure of which is incorporated by reference herein.

Thus, for example, a first amount of liquid polyethylene-polyepsilon caprolactone polymer mixture (50:50) is mixed with the adamantane derivative of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700: polyethylene in molten form is admixed with a high percentage of the adamantane derivative of our invention, having the structure:

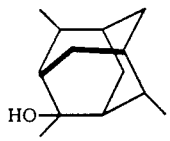

and the mixture is solidified in the form of pellets or beads. These pellets or beads thus contain a high percentage of adamantane derivative (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention, the adamantane derivative of our invention is added to the polymer in a large closed container or drum which is maintained under controlled temperature conditions while the polymer in a melted condition is mixed with the adamantane derivative of our invention under agitation.

In order that the perfume or flavor be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by the adamantane derivative of our invention is permitted to drip through the orifices onto a continuously moving, cooled conveyor upon which the polymer containing the adamantane derivative of our invention solidifies into small pellets with the perfume and/or flavor imprisoned therein. The apparatus useful in conjunction with this process advantageously includes a conveyor of a material which will not adhere to the polymer which contains the adamantane derivative of our invention.

In order that the droplets form into uniform pellets or beads, the conveyor is continuously washed with a liquid such as water to maintain the surface relatively cool. The pellets are delivered by the conveyor into a container and packaged for shipment or for further incorporation into articles of manufacture, e.g., garbage bags (using the deodorization quality of the adamantane derivative of our invention) or tobacco filters (using the tobacco flavoring or flavor enhancement properties of the adamantane derivative of our invention).

The following Example I sets forth preparation of the compound having the structure:

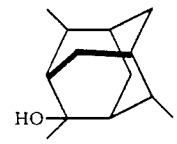

of our invention. Examples following Example I, e.g., Example II, et seq. serve to illustrate our invention as it is to be utilized.

The invention is considered to be restricted thereto only as indicated in the appended claims.

All parts and percentages given herein are by weight unless otherwise specified.

EXAMPLE I

PREPARATION OF 2,4,8-TRIMETHYL-2-ADAMANTANOL

Reactions:

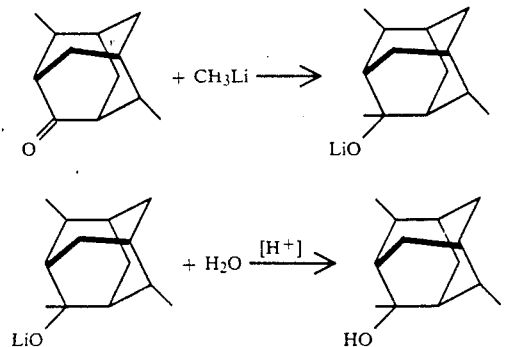

Into a 5 liter reaction vessel equipped with nitrogen blanket and cooling bath; reflux condenser and thermometer is placed 3200 ml of a solution of methyl lithium in diethyl ether (1.4 molar). The solution is blanketed with nitrogen and cooled to 0° C. While maintaining the reaction mass at 0° C., 454 grams of the compound having the structure:

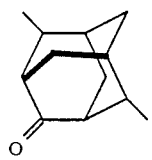

is added to the reaction mass over a period of 30 minutes dropwise.

The reaction mass temperature is then permitted to rise to room temperature with stirring over a period of 2 hours.

Methyl alcohol, toluene and water is then added to the reaction mass. The reaction mass is then washed with two volumes of water.

The reaction mass is then evaporated and is rushed over on a 4" splash column yielding the following fractions:

| Fraction No. | Vapor Temp (°C.) | Liquid Temp (°C.) | Vacuum mm/Hg. Pressure | Weight of Fraction (Grams) |
|---|---|---|---|---|
| 1 | 38 | 47 | 760 | 102.5 |
| 2 | 52 | 109 | 70 | 130.0 |
| 3 | 45 | 113 | 70 | 26.0 |
| 4 | 108 | 126 | 70 | 2.6 |
| 5 | 108 | 133 | 80 | 1.8 |
| 6 | 115 | 138 | 80 | 2.4 |
| 7 | 118 | 138 | 80 | 2.1 |
| 8 | 118 | 140 | 80 | 2.2 |

Fractions 5, 6, 7 and 8 are bulked and redistilled on a 1"×10" Goodloe column yielding the following fractions:

| Fraction No. | Vapor Temp. (°C.) | Liquid Temp. (°C.) | Vacuum mm/Hg. Pressure | Reflux Ratio | Weight of Fraction (Grams) |
|---|---|---|---|---|---|
| 1 | 102 | 118 | 28 | 9:1 | 10 |
| 2 | 98 | 118 | 1.0 | 9:1 | 7 |
| 3 | 99 | 120 | 1.0 | 9:1 | 7 |
| 4 | 99 | 121 | 1.4 | 9:1 | 10 |
| 5 | 100 | 120 | 1.8 | 9:1 | 10 |
| 6 | 100 | 121 | 1.8 | 9:1 | 19 |
| 7 | 100 | 121 | 1.2 | 4:1 | 14 |
| 8 | 107 | 120 | 1.2 | 4:1 | 7 |
| 9 | 99 | 115 | 1.8 | 4:1 | 7 |
| 10 | 97 | 115 | 1.8 | 9:1 | 10 |
| 11 | 96 | 115 | 1.4 | 9:1 | 12 |
| 12 | 96 | 114 | 1.5 | 9:1 | 5 |
| 13 | 97 | 115 | 1.4 | 9:1 | 4 |
| 14 | 99 | 121 | 1.5 | 4:1 | 25 |
| 15 | 99 | 123 | 1.7 | 4:1 | 40 |
| 16 | 98 | 124 | 1.5 | 4:1 | 48 |
| 17 | 98 | 125 | 1.5 | 4:1 | 39 |
| 18 | 99 | 126 | 1.5 | 4:1 | 19 |
| 19 | 99 | 129 | 1.02 | 4:1 | 39 |
| 20 | 94 | 130 | 0.924 | 4:1 | 17 |
| 21 | 93 | 139 | 0.880 | 4:1 | 25 |
| 22 | 93 | 185 | 0.954 | 4:1 | 16 |

Fractions 8 to 15 are bulked. Bulked fractions 8 to 15 have a pleasant fresh ginger and patchouli aroma profile, with patchouli, woody, spicy and ginger topnotes.

FIG. 1 is the GLC profile profile for the crude reaction mass prior to distillation.

FIG. 2 is the NMR spectrum for the compound having the structure:

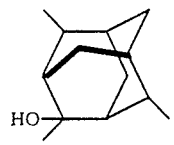

EXAMPLE II

PERFUME FORMULATION

The following "woody cologne" perfume formulation is prepared:

| Ingredients | Parts by Weight |
|---|---|
| Bergamot Oil | 150 |
| Orange oil | 200 |
| Lemon oil | 50 |
| Eugenol | 10 |
| Ylang oil | 42 |
| Petigrain Paraguay | 10 |
| Gamma methyl ionone | 20 |
| Vetiver Venezuela | 24 |
| The compound having the structure: 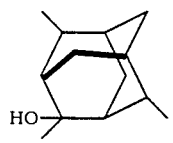 prepared according to Example I bulked distillation fractions 8-15. The compound having the structure: 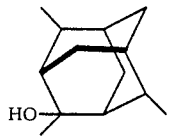 | 25 | produced according to Example I imparts to this woody cologne formulation fresh ginger and patchouli undertones and patchouli, woody, spicy and ginger topnotes. Accordingly, the perfume formulation can be described as: "cologne with fresh ginger and patchouli undertones and patchouli, woody, spicy and ginger topnotes"

EXAMPLE III

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| SUBSTANCE | AROMA DESCRIPTION |
|---|---|
| The compound having the structure: 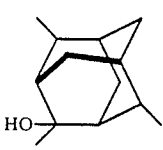 | A fresh, ginger and patchouli aroma with patchouli, woody, spicy and ginger topnotes. |

TABLE I-continued

| SUBSTANCE | AROMA DESCRIPTION |
| --- | --- |
| produced according to Example I, bulked fractions 8-15. | |
| Perfume composition of Example II. | A fresh, ginger and patchouli aroma with patchouli, woody, spicy and ginger topnotes. |

EXAMPLE IV

PERFUMED LIQUID DETERGENT

Concentrated liquid detergents with aromas as set forth in Table I of Example III (which detergents are prepared from Lysine salt of n-dodecyl benzene sulfonic acid as more specifically described in the U.S. Pat. No. 3,948,818 issued on Apr. 6, 1976, the specification for which is incorporated by reference herein) are prepared containing each of the substances set forth in Table I of Example III, supra. They are prepared by adding and homogeneously mixing the appropriate quantity of perfumery substance as set forth in Table I of Example III in the liquid detergent. The detergents all possess aromas as set forth in Table I of Example III, the intensity increasing with greater concentrations of perfumery substance of Table I of Example III, supra.

EXAMPLE V

PREPARATION OF A COLOGNE AND HANDKERCHIEF PERFUME

The perfume substances of Table I of Example III, supra, are incorporated into colognes at concentrations of 1.5%, 2.0%, 2.5%, 3.0% and 4.0% in 80%, 85% and 90% aqueous ethanol; and into a handkerchief perfume composition at concentrations of 10%, 15%, 20%, 25% and 30% (in 85%, 90% and 95% aqueous ethanol). Distinct and definitive aromas as set forth in Table I of Example III are imparted to the cologne and to the handkerchief perfume compositions.

EXAMPLE VI

PREPARATION OF A DETERGENT COMPOSITION

A total of 100 grams of a detergent powder (a non-ionic detergent powder containing a proteolytic enzyme prepared according to Example I of Canadian Letter Patent No. 985,190 issued on Mar. 9, 1976, the disclosure of which is incorporated by reference herein) is mixed with 0.15 grams of each of the substances until homogeneous compositions are obtained. These compositions have excellent aromas as set forth in Table I of Example III.

EXAMPLE VII

PREPARATION OF SOAP

Each of the perfumery substances of Table I of Example III are incorporated into soap (LVU-1) at 0.1% by weight of each substance. After two weeks in the oven at 90° F., each of the soaps showed no visual effect from the heat. Each of the soaps manifested an excellent aroma as set forth in Table I of Example III.

EXAMPLE VIII

PREPARATION OF SOAP COMPOSITION

One hundred grams of soap chips (IVORY ®, registered trademark of the Procter & Gamble Co. of Cincinnati, Ohio) are mixed individually with one gram each of the perfumery substances of Table I of Example III, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example III.

EXAMPLE IX

PREPARATION OF A SOLID DETERGENT COMPOSITION

A detergent is prepared from the following ingredients according to Example I of Canadian Letters Patent No. 1,007,948, the specification for which is incorporated by reference herein.

| Ingredients | Parts by Weight |
| --- | --- |
| "Neodol 45-11" (a$C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume substances of Table I of Example III, supra. The detergent samples each have excellent aromas as set forth in Table I of Example III, supra.

EXAMPLE X

Utilizing the procedure of Example I at column 15 of U.S. Pat. No. 3,632,396 (the specification for which is incorporated by reference herein), a non-woven cloth substrate useful as a dryer-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation m.p. about 150° F.); 57% $C_{20-22}$ HAPS; 22% isopropyl alcohol; 20% antistatic agent; 1% of one of the perfume substances of Table I of Example III, supra.

A fabric softening composition prepared as set forth above having the above aroma characteristics as set forth in Table I of Example III, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example III is imparted in a pleasant manner to the headspace in the dryer on operation thereof, using said dryer-added fabric softening non-woven fabric.

What is claimed is:

1. The compound having the structure:

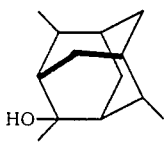

2. The process for augmenting or enhancing the aroma or taste of a consumable material selected from the group consisting of perfume compositions, perfumed articles, colognes, deodorants and odor maskants and tobacco compositions comprising the step of adding thereto an aroma or taste augmenting or enhancing quantity of the compound defined to claim 1.

3. The process of claim 2 wherein the consumable material is a perfume composition.

4. The process of claim 2 wherein the consumable material is a tobacco.

5. The process of claim 2 wherein the consumable material is an odor maskant.

6. The compound having the structure:

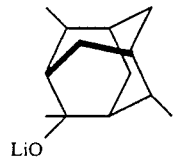

* * * * *